United States Patent
Takemoto et al.

(10) Patent No.: US 10,772,588 B2
(45) Date of Patent: Sep. 15, 2020

(54) PORTABLE RADIATION IMAGING APPARATUS

(71) Applicant: SHIMADZU CORPORATION, Kyoto (JP)

(72) Inventors: Hajime Takemoto, Kyoto (JP); Toru Hayakawa, Kyoto (JP)

(73) Assignee: SHIMADZU CORPORATION, Kyoto (JP)

( * ) Notice: Subject to any disclaimer, the term of this patent is extended or adjusted under 35 U.S.C. 154(b) by 0 days.

(21) Appl. No.: 16/476,303

(22) PCT Filed: Feb. 3, 2017

(86) PCT No.: PCT/JP2017/003895
§ 371 (c)(1),
(2) Date: Jul. 8, 2019

(87) PCT Pub. No.: WO2018/142557
PCT Pub. Date: Aug. 9, 2018

(65) Prior Publication Data
US 2019/0350544 A1    Nov. 21, 2019

(51) Int. Cl.
*A61B 6/00* (2006.01)
(52) U.S. Cl.
CPC .............. *A61B 6/4405* (2013.01); *A61B 6/56* (2013.01)
(58) Field of Classification Search
None
See application file for complete search history.

(56) References Cited

U.S. PATENT DOCUMENTS

| | | | |
|---|---|---|---|
| 8,459,868 B2 * | 6/2013 | Boomgaarden | A61B 6/4405 378/198 |
| 8,532,260 B2 * | 9/2013 | Takae | A61B 6/4405 378/102 |
| 8,705,699 B2 * | 4/2014 | Fuse | A61B 6/4405 378/102 |

(Continued)

FOREIGN PATENT DOCUMENTS

JP    2007289408    11/2007

OTHER PUBLICATIONS

"International Search Report (Form PCT/ISA/210)" of PCT/JP2017/003895, dated Apr. 4, 2017, with English translation thereof, pp. 1-4.

(Continued)

*Primary Examiner* — Thomas R Artman
(74) *Attorney, Agent, or Firm* — JCIPRNET

(57) ABSTRACT

A chassis has a structure in which a front structure and a rear structure are linked by an upper floor and a lower floor. The front structure is linked to a front wheel via a coupling member, a front wheel support member and a shaft. The front structure has a cylindrical support member. In addition, the rear structure is linked to a rear wheel via a shaft. A reinforcing member, which links the front structure and the rear structure in the central part of a space for accommodating a battery, is installed inside the space for accommodating the battery. The front end of the reinforcing member is linked to the cylindrical support member in the front structure. The upper surface of the reinforcing member is fixed to the upper floor and the lower surface of the reinforcing member is fixed to the lower floor.

6 Claims, 4 Drawing Sheets

(56) References Cited

U.S. PATENT DOCUMENTS

| | | | | |
|---|---|---|---|---|
| 9,198,270 B2* | 11/2015 | Chicchetti | | H05G 1/08 |
| 10,058,303 B2* | 8/2018 | Shimohira | | A61B 6/06 |
| 2005/0135560 A1* | 6/2005 | Dafni | | A61B 6/56 |
| | | | | 378/101 |
| 2011/0110498 A1* | 5/2011 | Takae | | G01R 31/3693 |
| | | | | 378/102 |
| 2012/0008748 A1* | 1/2012 | Fuse | | A61B 6/4405 |
| | | | | 378/98 |
| 2012/0128130 A1* | 5/2012 | Boomgaarden | | A61B 6/102 |
| | | | | 378/198 |
| 2014/0098939 A1* | 4/2014 | Yamanaka | | A61B 6/56 |
| | | | | 378/62 |
| 2015/0305699 A1* | 10/2015 | Sakuragi | | A61B 6/4405 |
| | | | | 250/493.1 |
| 2017/0020479 A1* | 1/2017 | Shimohira | | A61B 6/4405 |
| 2019/0350544 A1* | 11/2019 | Takemoto | | A61B 6/56 |

OTHER PUBLICATIONS

"Written Opinion (Form PCT/ISA/237)" of PCT/JP2017/003895, dated Apr. 4, 2017, with English translation thereof, pp. 1-4.

* cited by examiner

PORTABLE RADIATION IMAGING APPARATUS

CROSS-REFERENCE TO RELATED APPLICATION

This application is a 371 application of the International PCT application serial no. PCT/JP2017/003895, filed on Feb. 3, 2017. The entirety of the above-mentioned patent application is hereby incorporated by reference herein and made a part of this specification.

BACKGROUND

Technical Field

The invention relates to a portable radiation imaging apparatus.

Description of Related Art

A portable X-ray imaging apparatus, which is one type of such a portable radiation imaging apparatus, is also called a round-visit X-ray imaging apparatus and is moved between the patients' rooms for X-ray imaging. The portable X-ray imaging apparatus includes a main body with front wheels and rear wheels, a support disposed upright on the main body, an elevating member moving up or down along the support while supporting an X-ray irradiation part which includes an X-ray tube and a collimator, an X-ray detector for detecting the X-ray emitted from the X-ray irradiation part and passing through the examinee, and a battery disposed inside the main body.

In such a portable X-ray imaging apparatus, the battery disposed in the main body is the source of power for driving the wheels to move the portable X-ray imaging apparatus and power for emitting an X-ray from the X-ray tube. The power is stored in advance in the battery from the external power supply via a power supply cord and a charging circuit (see Patent Document 1).

RELATED ART

Patent Document

[Patent Document 1] Japanese Laid-Open No. 2007-289408

SUMMARY

Problems to be Solved

Since such a portable X-ray imaging apparatus needs to be moved between wards for performing X-ray imaging continuously, the battery disposed inside the main body has become large and its weight also increases. Therefore, there is a demand for accommodating the battery inside a chassis that constitutes the main body of the portable X-ray imaging apparatus.

When the battery is accommodated in the chassis, generally the battery is disposed between the front wheel and the rear wheel. However, when the portable X-ray imaging apparatus travels, the front wheel and the rear wheel may receive impact from the floor surface due to unevenness of the floor surface, and a force in a twisting direction may be applied to the chassis. When this force causes the chassis to twist, problems occur. That is, the support disposed upright on the main body shakes, and the elevating member linked to the support and the X-ray irradiation part supported by the elevating member shake greatly.

The invention has been made solve the above-mentioned problems, and the invention aims to provide a portable radiation imaging apparatus that can prevent the elevating member and the radiation irradiation part from shaking and can travel stably even when the battery is accommodated in the chassis.

According to one aspect of the invention, in a portable radiation imaging apparatus including a main body having front wheels and rear wheels, a support disposed upright on the main body, an elevating member moving up or down along the support while supporting a radiation irradiation part, and batteries disposed inside the main body, a chassis that constitutes the main body includes: a front structure linked to the front wheels; a rear structure linked to the rear wheels; a floor linking the front structure and the rear structure in a state where a space for accommodating the batteries is formed between the front structure and the rear structure and openings are formed on left and right sides of the space; and a reinforcing member linking the front structure and the rear structure in a central region of the space that is for accommodating the batteries, wherein a plurality of batteries are accommodated in the space from the openings formed on the left and right sides of the space that is for accommodating the batteries.

According to another aspect of the invention, the front structure and the rear structure are linked by an upper floor disposed on an upper portion of the batteries and a lower floor disposed on a lower portion of the batteries, and the reinforcing member is fixed to at least one of the upper floor and the lower floor.

According to another aspect of the invention, the reinforcing member has a hollow shape.

According to another aspect of the invention, the front structure includes a cylindrical support member for supporting the support to be rotatable around a vertical axis, and the reinforcing member is linked to the cylindrical support member.

According to the above description, the action of the reinforcing member that links the front structure and the rear structure in the central region of the space for accommodating the batteries can prevent the elevating member and the radiation irradiation part from shaking even when the batteries are accommodated in the chassis. Thus, it is possible for the portable radiation imaging apparatus to travel stably.

According to the above description, since the reinforcing member is fixed to the upper floor and/or the lower floor, it is possible to increase the twisting rigidity with the action of the floor and the reinforcing member.

According to the above description, it is possible to reduce the weight of the reinforcing member while increasing the rigidity of the reinforcing member.

According to the above description, it is possible to further increase the twisting rigidity with the action of the cylindrical support member and the reinforcing member.

DESCRIPTION OF THE EMBODIMENTS

Figure 1:
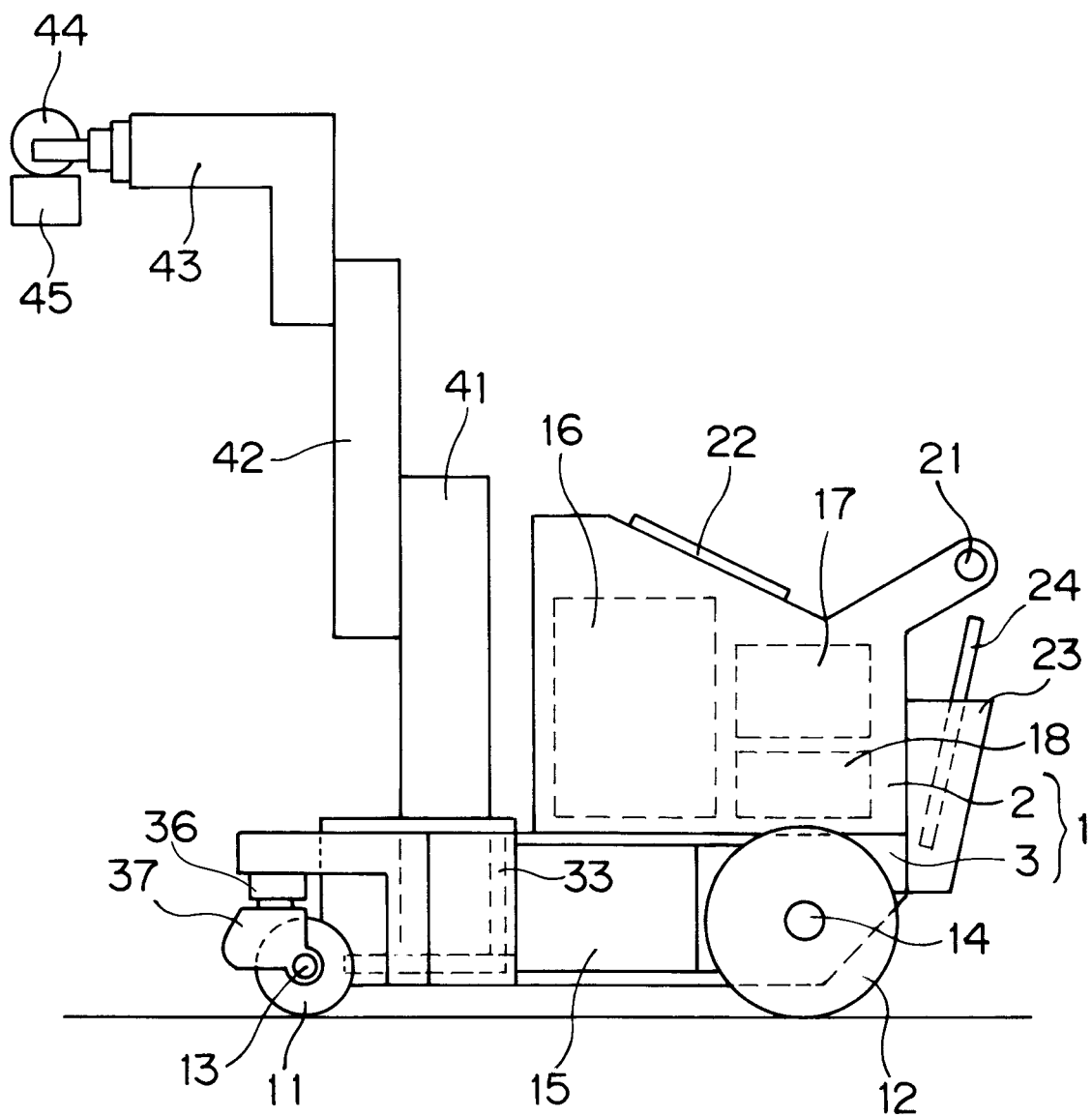
FIG. 1 is a schematic view of a portable X-ray imaging apparatus that serves as the portable radiation imaging apparatus according to the invention.

Hereinafter, an embodiment of the invention will be described with reference to the drawings. FIG. 1 is a schematic view of a portable X-ray imaging apparatus that serves as the portable radiation imaging apparatus according to the invention.

The portable X-ray imaging apparatus includes a main body 1 that is composed of a body 2 and a chassis 3. On the front side in the traveling direction of the chassis 3 of the portable X-ray imaging apparatus, a pair of left and right front wheels 11, which are wheels for changing the direction, are disposed to be rotatable around a shaft 13 via a rotatable link member 36 and a front wheel support member 37. Further, on the rear side in the traveling direction of the chassis 3 of the portable X-ray imaging apparatus, a pair of left and right rear wheels 12, which are wheels for driving, are disposed to be rotatable around a pair of left and right shafts 14 that are driven by a motor (not shown) to rotate individually. In addition, batteries 15 are disposed at positions between the front wheels 11 and the rear wheels 12 on the chassis 3.

On the front side in the traveling direction of the chassis 3 that constitutes the main body 1, a support 41 is disposed upright, and a first elevating member 42 and a second elevating member 43 are disposed on the support 41 so as to move up or down. The second elevating member 43 has a substantially L shape in the side view, and an X-ray irradiation part including an X-ray tube 44 and a collimator 45 is disposed at the front end of the second elevating member 43. The X-ray tube 44 and the collimator 45 move up or down as the first elevating member 42 and the second elevating member 43 move up or down. The lower end portion of the support 41 has a columnar shape and is supported by a cylindrical support member 33 formed in the chassis 3 to be rotatable around a vertical axis. The X-ray tube 44 and the collimator 45 rotate together with the second elevating member 43 as the support 41 rotates.

An operation handle 21 for operating the traveling direction of the main body 1, an LCD touch panel 22 functioning as a display part and an operation part, and a housing part 23 for accommodating an X-ray detector 24 such as a flat panel detector for detecting the X-ray emitted from the X-ray tube 44 and passing through the examinee are disposed on the body 2 that constitutes the main body 1. Further, a high voltage part 16 for supplying a high voltage to the X-ray tube 44, an image processing part 17 for processing an X-ray image detected by the X-ray detector 24, and a motor control part 18 for controlling the motor that drives the rear wheels 12 are disposed inside the body 2.

Figure 2:
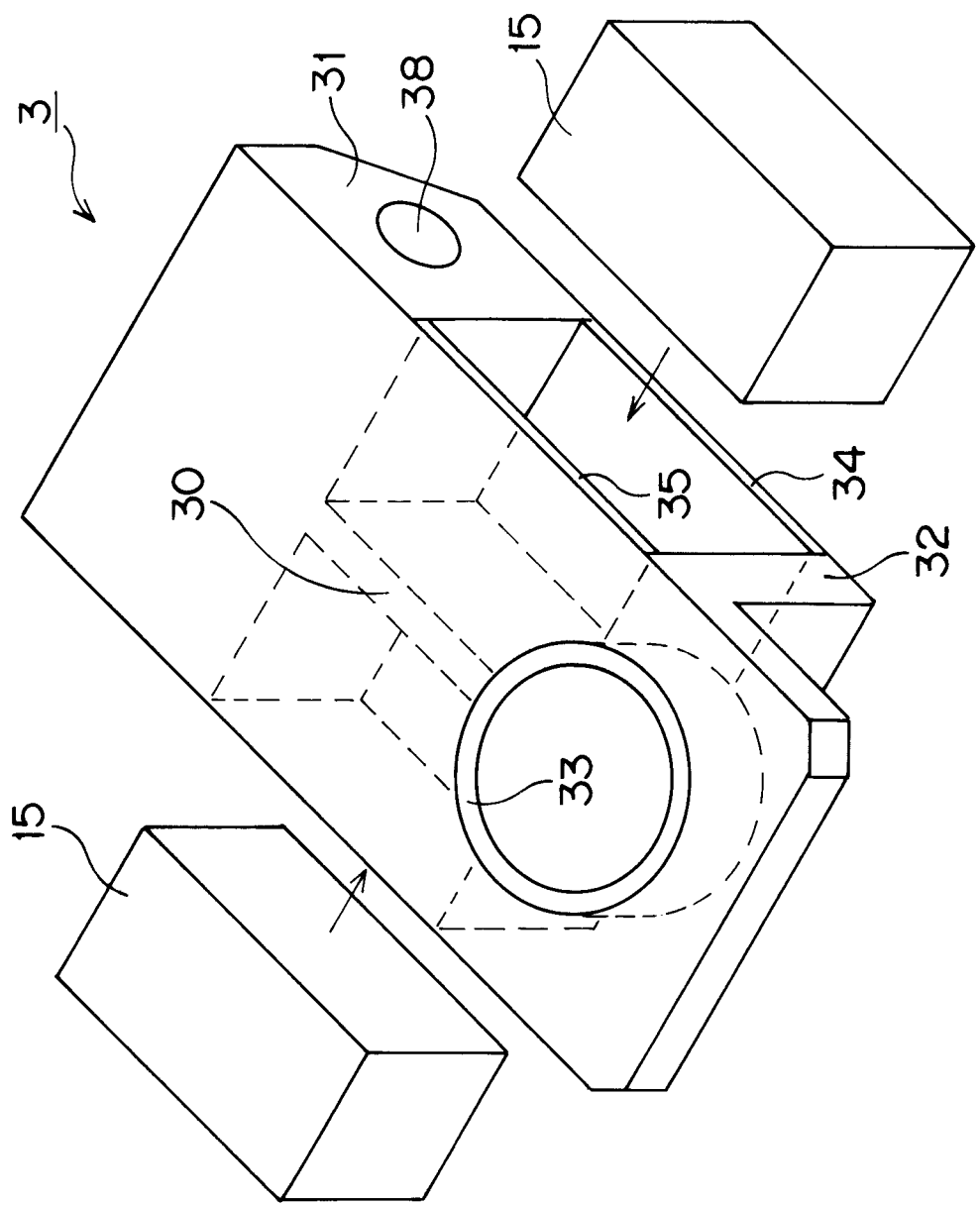
FIG. 2 is a perspective view showing the chassis 3 together with the batteries 15.

FIG. 2 is a perspective view showing the chassis 3 that constitutes the main body 1 together with the batteries 15.

The chassis 3 has a structure in which a front structure 32 and a rear structure 31 are linked by an upper floor 35 and a lower floor 34. The front structure 32 is linked to the front wheels 11 via the link member 36, the front wheel support member 37, and the shaft 13 described above. The front structure 32 has the above-mentioned cylindrical support member 33. Further, the rear structure 31 is formed with a hole 38 for attaching a speed reducer and the motor to which the rear wheels 12 are attached, so that the rear structure 31 is linked to the rear wheels 12.

The upper floor 35 and the lower floor 34 form a space that can accommodate a pair of batteries 15 between the front structure 32 and the rear structure 31, and link the front structure 32 and the rear structure 31 in a state where openings are formed on the left and right sides of the space. Thus, the space for accommodating the batteries 15 is formed by the upper floor 35, the lower floor 34, the front structure 32, and the rear structure 31. Then, a reinforcing member 30 that links the front structure 32 and the rear structure 31 in the central part of the accommodating space of the batteries 15 is disposed in the accommodating space of the batteries 15.

Figure 3:
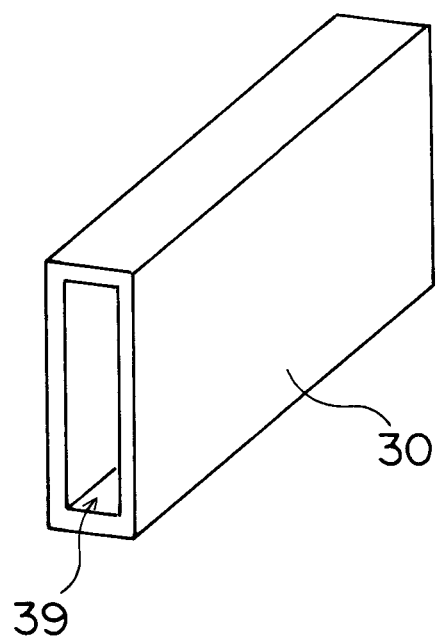
FIG. 3 is a perspective view of the reinforcing member 30.

FIG. 3 is a perspective view of the reinforcing member 30.

The reinforcing member 30 has a hollow shape made of a metal plate with a space 39 formed inside. By making the metal plate into a hollow shape, it is possible to reduce the weight while increasing the rigidity. The front end of the reinforcing member 30 is linked to the cylindrical support member 33 in the front structure 32. Moreover, the rear end of the reinforcing member 30 is linked to the rear structure 31. Also, the upper surface of the reinforcing member 30 is fixed to the upper floor 35. Furthermore, the lower surface of the reinforcing member 30 is fixed to the lower floor 34.

In the portable X-ray imaging apparatus having the above configuration, when the batteries 15 are installed in the main body 1, the side of the main body 1 and the side of the pair of batteries 15 are electrically connected by a connector or the like (not shown), and then each of the batteries 15 is accommodated in the accommodating space from the openings formed on the left and right sides of the accommodating space of the batteries 15 in the chassis 3. Thus, it is possible to accommodate large and heavy batteries 15 inside the chassis 3 under the main body 1 of the portable X-ray imaging apparatus. Since the heavy batteries 15 can be disposed under the main body 1, the portable X-ray imaging apparatus can travel stably.

At this time, since the configuration accommodates the pair of batteries 15 in the accommodating space via the openings formed on the left and right sides of the accommodating space of the batteries 15, even if the high voltage part 16, the image processing part 17, the motor control part 18, etc. are disposed in the body 2 of the main body 1, the batteries 15 can be installed or replaced without removing these members.

Figure 4:
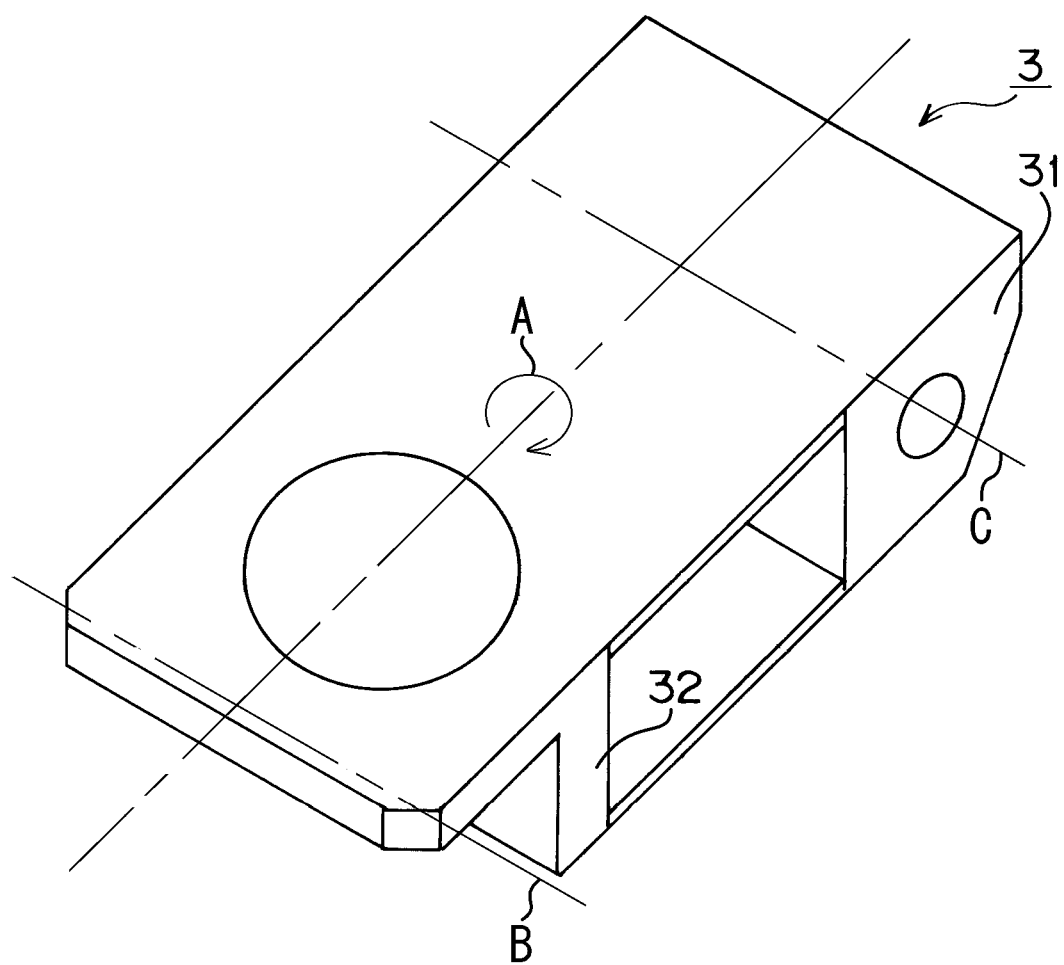
FIG. 4 is an explanatory view showing a state when a twist occurs.

FIG. 4 is an explanatory view showing a state when a twist occurs to the chassis 3.

When the portable X-ray imaging apparatus described above travels, the pair of front wheels 11 and the pair of rear wheels 12 receive impact from the floor surface due to unevenness of the floor surface, and a force in a twisting direction is applied to the chassis 3. Thus, a force is applied to the chassis 3 to cause a twist around an axis that is in a direction orthogonal to the line B which connects the input points from the front wheels 11 (the points where the force to the front wheels 11 acts on the chassis 3) and the line C that connects the input points from the rear wheels 12 (the points where the force to the rear wheels 12 acts on the chassis 3), as indicated by the arrow A in FIG. 4. However, for the portable X-ray imaging apparatus according to the invention, the occurrence of twisting to the chassis 3 is suppressed by the action of the reinforcing member 30 that links the front structure 32 and the rear structure 31. Therefore, it is possible to suppress the support 41 from shaking and prevent the first and second elevating members 42 and 43, the X-ray tube 44, and the collimator 45 from shaking greatly for the portable X-ray imaging apparatus to travel stably.

Particularly, in the portable X-ray imaging apparatus described above, the upper surface of the reinforcing member 30 is fixed to the upper floor 35 and the lower surface of the reinforcing member 30 is fixed to the lower floor 34. Therefore, the upper floor 35, the lower floor 34, and the reinforcing member 30 form a structure having a substantially H-shaped cross section and can effectively prevent the chassis 3 from twisting.

Furthermore, in the portable X-ray imaging apparatus described above, the front end of the reinforcing member 30 is linked to the cylindrical support member 33 in the front structure 32. The cylindrical support member 33 is usually made of a metal cylindrical member that has a diameter of 30 cm or more, and it is a very strong structure against a twist in the direction of the arrow A shown in FIG. 4. Thus, it is possible to more effectively prevent the chassis 3 from twisting.

In the above-described embodiment, the reinforcing member 30 is disposed in the central part of the accommodating space of the batteries 15. However, the position of the reinforcing member 30 may be moved from the central part to the left or right to a certain extent as long as it is in the central region of the space where the batteries 15 can be accommodated. For example, in the above-described embodiment, a pair of batteries 15 of the same size are accommodated from the openings formed on both sides of the accommodating space of the batteries 15. However, if the pair of batteries 15 has different sizes, the arrangement of the reinforcing member 30 may be moved from the central part to the left or right. In addition, for example, even if two batteries are accommodated from the right side and three batteries are accommodated from the left side, the position of the reinforcing member 30 may be moved from the central part of the space where the batteries can be accommodated to the left or right. The reinforcing member 30 may be disposed in the central region of the space where the batteries can be accommodated. Further, the battery 15 may be an aggregate of a plurality of batteries instead of one single battery.

Furthermore, in the above-described embodiment, the reinforcing member 30 is fixed to both the upper floor 35 and the lower floor 34. However, it may be fixed to one of the upper floor 35 and the lower floor 34. In addition, if sufficient strength can be obtained, it is also possible to adopt a configuration in which the reinforcing member 30 is not fixed to the upper floor 35 and the lower floor 34.

Besides, in the above-described embodiment, the X-ray irradiation part including the X-ray tube 44 and the collimator 45 is moved up or down by the first elevating member 42 and the second elevating member 43. However, instead of using the first elevating member 42 and the second elevating member 43, one single elevating member or three or more elevating members may be used to move up or down the X-ray irradiation part.

Furthermore, in the above-described embodiment, the X-ray irradiation part including the X-ray tube 44 and the collimator 45 is supported by the second elevating member 43 that has a substantially L shape in the side view. However, a member in any other shape may be used as the support member for supporting the X-ray irradiation part.

What is claimed is:

1. A portable radiation imaging apparatus, comprising a main body having front wheels and rear wheels, a support disposed upright on the main body, an elevating member moving up or down along the support while supporting a radiation irradiation part, and batteries disposed inside the main body, wherein:
   a chassis that constitutes the main body comprises:
   a front structure linked to the front wheels;
   a rear structure linked to the rear wheels;
   a floor linking the front structure and the rear structure in a state where a space for accommodating the batteries is formed between the front structure and the rear structure and openings are formed on left and right sides of the space; and
   a reinforcing member linking the front structure and the rear structure in a central region of the space that is for accommodating the batteries,
      wherein a plurality of batteries are accommodated in the space from the openings formed on the left and right sides of the space that is for accommodating the batteries.

2. The portable radiation imaging apparatus according to claim 1, wherein the front structure and the rear structure are linked by an upper floor disposed on an upper portion of the batteries and a lower floor disposed on a lower portion of the batteries, and
   the reinforcing member is fixed to at least one of the upper floor and the lower floor.

3. The portable radiation imaging apparatus according to claim 2, wherein the reinforcing member has a hollow shape.

4. The portable radiation imaging apparatus according to claim 3, wherein the front structure comprises a cylindrical support member for supporting the support to be rotatable around a vertical axis, and
   the reinforcing member is linked to the cylindrical support member.

5. The portable radiation imaging apparatus according to claim 2, wherein the front structure comprises a cylindrical support member for supporting the support to be rotatable around a vertical axis, and
   the reinforcing member is linked to the cylindrical support member.

6. The portable radiation imaging apparatus according to claim 1, wherein the front structure comprises a cylindrical support member for supporting the support to be rotatable around a vertical axis, and
   the reinforcing member is linked to the cylindrical support member.

* * * * *